(12) United States Patent
Miyamoto

(10) Patent No.: US 9,517,039 B2
(45) Date of Patent: Dec. 13, 2016

(54) X-RAY MEASUREMENT ASSISTING TOOL

(71) Applicant: HITACHI ALOKA MEDICAL, LTD., Tokyo (JP)

(72) Inventor: Takahiro Miyamoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 52 days.

(21) Appl. No.: 14/440,664

(22) PCT Filed: Oct. 22, 2013

(86) PCT No.: PCT/JP2013/078514
§ 371 (c)(1),
(2) Date: May 5, 2015

(87) PCT Pub. No.: WO2014/073364
PCT Pub. Date: May 15, 2014

(65) Prior Publication Data
US 2015/0282771 A1 Oct. 8, 2015

(30) Foreign Application Priority Data
Nov. 8, 2012 (JP) .................. 2012-246544

(51) Int. Cl.
*A61B 6/04* (2006.01)
*H01J 37/28* (2006.01)
(Continued)

(52) U.S. Cl.
CPC ............... *A61B 6/04* (2013.01); *A61B 6/107* (2013.01); *A61B 6/505* (2013.01); *A61G 13/123* (2013.01);
(Continued)

(58) Field of Classification Search
CPC ....... A61B 6/0421; A61B 6/0442; A61B 6/04; A61B 5/0555; A61B 5/4528; A61G 13/12; A61G 13/1245; A61G 13/1295; H01J 37/28
(Continued)

(56) References Cited

U.S. PATENT DOCUMENTS 5,085,214 A * 2/1992 Barrett ...................... A61F 5/01
128/882
5,657,369 A * 8/1997 Stein .................... A61B 6/0421
378/195

(Continued)

FOREIGN PATENT DOCUMENTS

| CA | 1217578 A | 2/1987 |
| JP | 1-223939 A | 9/1989 |

(Continued)

OTHER PUBLICATIONS

European Search Report dated Nov. 13, 2015 issued in counterpart European Patent Application No. 13853906.9. (7 pages).

(Continued)

*Primary Examiner* — David A Vanore
(74) *Attorney, Agent, or Firm* — Westerman, Hattori, Daniels & Adrian, LLP

(57) ABSTRACT

This assisting tool is a multi-functional tool that is used in X-ray measurements of a subject. The multi-functionality is achieved by using the outer form and the inner structure of the tool in combination. More specifically, this assisting tool has two inclined surfaces that constitute the outer form. By inserting this assisting tool under the two legs, the two legs can be kept in a posture in which the knees are bent. The side end structure that constitutes the outer form keeps the two feet in a twisted state. A measurement chamber that constitutes the inner structure is for measuring the forearm.

14 Claims, 6 Drawing Sheets

(51) Int. Cl.
*A61B 5/05* (2006.01)
*A61B 6/10* (2006.01)
*A61G 13/12* (2006.01)
*A61B 6/00* (2006.01)

(52) U.S. Cl.
CPC ......... *A61G 13/125* (2013.01); *A61G 13/1235* (2013.01); *A61G 13/1245* (2013.01); *A61B 6/482* (2013.01); *A61G 2210/50* (2013.01)

(58) Field of Classification Search
USPC ............... 128/869, 882, 878; 600/421, 415; 378/195, 208, 209
See application file for complete search history.

(56) References Cited

U.S. PATENT DOCUMENTS

| | | | | |
|---|---|---|---|---|
| 5,662,121 | A * | 9/1997 | Zucker | A61B 5/103 600/587 |
| 5,748,704 | A | 5/1998 | Mazess et al. | |
| 6,047,083 | A * | 4/2000 | Mizuno | G01N 23/2251 257/E21.525 |
| 6,067,164 | A * | 5/2000 | Onoguchi | H01J 37/265 250/310 |
| 6,099,489 | A * | 8/2000 | Herzberg | A61F 5/3738 128/876 |
| 6,373,054 | B2 * | 4/2002 | Hiroi | H01J 37/304 250/307 |
| 7,098,660 | B2 * | 8/2006 | Contrada | A61B 5/0555 324/309 |
| 7,394,256 | B2 * | 7/2008 | Schubert | G01R 33/34046 324/307 |
| 7,947,862 | B2 * | 5/2011 | Livorsi | A61B 17/135 128/845 |
| 8,082,924 | B2 * | 12/2011 | Fischer | A61B 6/04 128/869 |
| 8,190,236 | B2 * | 5/2012 | Prince | A61B 17/1322 600/415 |
| 9,285,440 | B2 * | 3/2016 | Driemel | G01R 33/34007 |
| 2002/0077539 | A1 * | 6/2002 | Schmit | A61B 6/0442 600/410 |
| 2002/0092530 | A1 * | 7/2002 | Chapman | A61F 5/3723 128/878 |
| 2003/0121525 | A1 * | 7/2003 | Chapman | E05B 75/00 128/878 |
| 2004/0093673 | A1 * | 5/2004 | Marshall | A61B 6/0421 5/650 |
| 2004/0127786 | A1 | 7/2004 | Schmit et al. | |
| 2010/0078034 | A1 | 4/2010 | Fischer et al. | |
| 2016/0172154 | A1 * | 6/2016 | Kakinuma | H01J 37/28 250/306 |

FOREIGN PATENT DOCUMENTS

| | | |
|---|---|---|
| JP | 2004-16392 A | 1/2004 |
| JP | 2010-516311 A | 5/2010 |

OTHER PUBLICATIONS

Notification of Transmittal of Translation of the International Preliminary Report on Patentabililty (Form PCT/IB/338) of International Application No. PCT/JP2013/078514 mailed May 21, 2015 with Forms PCT/IB/373, PCT/IB/326 and PCT/ISA/237, with translation. (10 pages).

International Search Report dated Nov. 19, 2013 issued in corresponding application No. PCT/JP2013/078514.

* cited by examiner

X-RAY MEASUREMENT ASSISTING TOOL

TECHNICAL FIELD

The present invention relates to an X-ray measurement supporting tool, and in particular, to an X-ray measurement supporting tool which is placed on a bed and which fixes an orientation of a limb of a subject.

BACKGROUND ART

In general imaging, bone density measurement, or the like by radiation of an X-ray to a subject, a supporting tool is used as necessary. When the lumbar spine is to be measured, in general, the subject is laid face-up on an imaging stage. In this case, an orientation with bent knees of both legs is desired. In the orientation with the bent knees, the lumbar spine can be stretched out, resulting in a reduced degree of curvature of the lumbar spine. In the related art, in order to cause such a knee-bent orientation to be taken naturally; more specifically, in order to set an inclination angle of the thigh with respect to the bed surface to be an angle of greater than or equal to 45 degrees, a supporting tool dedicated for lumbar spine measurement such as a cushion having a trapezoidal or triangular cross section is inserted below the knee (refer to Patent Document 1).

When the femur is to be measured also, the subject is laid face-up on the imaging stage. In this case, it is desired that the legs be twisted such that the toes of the feet are rotated inward (toes moved close to the toes of the other foot). In order to create and maintain such a twisted orientation, a supporting tool dedicated for the measurement of the femur is used. The supporting tool has two inclined surfaces sandwiched between the legs. The inner sides of the legs are caused to contact the inclined surfaces, to achieve the twisted orientation of the legs. In order to maintain the twisted orientation, the legs are fixed by a belt or the like.

When an antebrachial bone (primarily, the radius) is to be measured, a supporting tool dedicated for the antebrachial bone measurement is placed on the imaging stage, which has a grip gripped by the subject (refer to Patent Document 2). With the use of such a supporting tool, the forearm is placed horizontally on the imaging stage. In this state, an X-ray is radiated onto the forearm.

RELATED ART REFERENCES

Patent Documents

[Patent Document 1] JP H1-223939 A
[Patent Document 2] JP 2004-16392 A

DISCLOSURE OF INVENTION

Technical Problem

As described, in the related art, a dedicated supporting tool is prepared for each measurement target site, and the supporting tool must be replaced when the measurement target site differs from the previous measurement target site. This has resulted in complexity and also a necessity for securing a large storage space for storing a plurality of types of the supporting tools.

An advantage of the present invention is that a multi-functional supporting tool is realized. Another advantage of the present invention is that it becomes possible to fix a plurality of sites of a subject with one supporting tool.

Solution to Problem (1) According to one aspect of the present invention, there is provided an X-ray measurement supporting tool comprising: an outer form that maintains, when a first bone part of a subject is to be measured, a first limb of the subject in a first orientation; and an inner structure that maintains, when a second bone part of the subject is to be measured, a second limb of the subject in a second orientation.

According to the above-described structure, multiple functions can be realized using both an outer form and an inner structure of the supporting tool. In other words, the structure uses not only the outer side of the supporting tool, but also the inner side of the supporting tool. As the outer form, the entire supporting tool may be used, or a part of the supporting tool (for example, an end) may be used. Alternatively, both the entire tool and the part of the tool may be used. In the related art, the inner side of the supporting tool has not been used, and is a dead space. However, with the above-described structure, such a space can be effectively used. With this configuration, a multi-functional supporting tool that can selectively fix a plurality of limbs can be realized. That is, it becomes unnecessary to replace the supporting tool when the measurement target site is changed. Consequently, the inspection time can be shortened. In addition, because it is not necessary to prepare a plurality of types of the supporting tools, a large storage space becomes no longer necessary.

The above-described supporting tool can be used for general X-ray imaging, and also in bone density measurement. In the latter case, the measurement target sites (first bone part, second bone part) are, for example, the lumbar spine, the femur, the radius, or the like. Alternatively, other bones may be set as the measurement target. Fixation target sites (first limb, second limb) are, for example, a lower limb and an upper limb. Alternatively, two lower limbs may be simultaneously fixed. Various fixation methods may be selectively used so long as the orientation of the limb can be maintained. For example, a method of constraining the limb so that the limb cannot move may be employed, or a method of simply supporting the formation and maintenance of the orientation of the limb may be employed. According to another aspect of the present invention, preferably, the first limb is a lower limb, and the second limb is an upper limb. According to such a configuration, the lower limb and the upper limb can be sequentially fixed with a single supporting tool.

According to another aspect of the present invention, preferably, the second bone part is a radius, the inner structure has a measurement chamber into which a forearm serving as the upper limb is inserted, and a scattering X-ray shielding member that blocks a scattering X-ray generated in the measurement chamber is provided on at least a part of a periphery of the measurement chamber. According to such a configuration, the inner structure has the measurement chamber, and in a state where the forearm is inserted into the measurement chamber and the orientation of the forearm is maintained, X-ray measurement of the forearm can be executed. When the X-ray is radiated onto the bone in the forearm, scattering of the X-ray is caused in the bone. According to the above-described configuration, the scattering X-ray is blocked by the scattering X-ray shielding member, and therefore, leakage of the scattering X-ray from the measurement chamber to the outside can be reduced, and radiation exposure of the subject can be reduced.

According to another aspect of the present invention, preferably, the inner structure has a base equipped with a grip gripped by the subject, and a measurement X-ray shielding member for preventing excessive radiation exposure is provided on an outside of a measurement region in the base. According to such a configuration, by placing the forearm on the base in a state of gripping the grip, the orientation of the forearm can be maintained. On the base, a measurement region into which the measurement site enters and a non-measurement region which is the region other than the measurement region are set. By providing the measurement X-ray shielding member in a part of the non-measurement region or the whole non-measurement region, the X-ray existing on the measurement X-ray shielding member and directed toward the non-measurement site can be blocked, or the intensity of the X-ray can be weakened, resulting in prevention or reduction of unnecessary radiation exposure of the subject. Alternatively, the whole base may be formed with an X-ray weakening member. In this case, the X-ray intensity can be reduced during the forearm measurement, and saturation at an X-ray detector can be prevented.

According to another aspect of the present invention, preferably, the inner structure has a height varying structure that allows a mounting height of the base to be varied. According to such a configuration, when the X-ray beam has a spreading shape; that is, when the X-ray beam is a fan-beam of a cone-beam, a magnification may be varied. According to another aspect of the present invention, preferably, a transparent top plate is provided above the measurement chamber. According to such a configuration, an inside of the measurement chamber can be observed from above, through the top plate. With this configuration, it can be easily confirmed that the measurement site is at a proper position, and a feeling of safety can be given to the subject.

According to another aspect of the present invention, preferably, the first bone part is the lumbar spine, the first orientation is a knee-bent orientation of a lower limb serving as the first limb, and the outer form has a form supporting the knee-bent orientation of the lower limb. According to such a configuration, the supporting tool can be provided below the lower limb, and the knee-bent orientation of the lower limb is formed and maintained by the supporting tool. According to another aspect of the present invention, preferably, the X-ray measurement supporting tool further comprises: a first inclined surface that contacts a back side of a thigh of the subject in a state where the knee-bent orientation of the lower limb is supported; and a second inclined surface that contacts a calf of the subject in a state where the knee-bent orientation of the lower limb is supported. According to another aspect of the present invention, preferably, the X-ray measurement supporting tool has a vertical cross section of a trapezoid.

According to another aspect of the present invention, preferably, the first bone part is a femur, the first limb is a lower limb, and the outer form comprises: a recess that houses a heel of the lower limb; an inclined surface to which an inner side surface of the lower limb from a region near an ankle to a joint of a big toe is caused to contact and that sets the lower limb in a twisted orientation; and a fixation member that fixes the lower limb in the twisted orientation from the heel toward a side of a toe. According to such a configuration, a distant end of the lower limb from the heel to the toe is fixed by the outer form. More specifically, the heel at the distant end is placed in the recess, and the inner side surface of the distant end is caused to contact the inclined surface. The contact state is maintained by the fixation member. In other words, the twisted orientation is forcefully formed and maintained.

According to another aspect of the present invention, preferably, the first bone part is a left femur and a right femur, the first limb is a left lower limb and a right lower limb, and the outer form comprises: a first recess and a second recess that house a left heel and a right heel of the left lower limb and the right lower limb, respectively; a first inclined surface and a second inclined surface to which a left inner side surface and a right inner side surface of the left lower limb and the right lower limb from regions near a left ankle and a right ankle to joints of a left big toe and a right big toe are caused to contact, respectively, and that set the left lower limb and the right lower limb in a twisted orientation, respectively; and a first fixation member and a second fixation member that fix the left lower limb and the right lower limb in the twisted orientation from the left heel and the right heel toward a side of a left toe and a side of a right toe, respectively. According to such a configuration, two distant ends of two lower limbs can be fixed in the twisted orientation. Preferably, the outer form is provided on one end of the supporting tool. In this case, an opening in communication with the measurement chamber is preferably formed on the other end. In other words, with the use of a front surface, a rear surface, the one end, the other end, and the inside of the supporting tool, it is possible to eliminate wasteful space and a wasteful region, and to realize a high-function supporting tool having a compact size.

(2) According to another aspect of the present invention, there is provided an X-ray measurement supporting tool comprising: a first outer form that maintains, when a lumbar spine of a subject is to be measured, a lower limb of the subject in a knee-bent orientation; a second outer form that maintains, when a femur of the subject is to be measured, the lower limb of the subject in a twisted orientation; and an inner structure that maintains, when an antebrachial bone of the subject is to be measured, a forearm of the subject in a horizontal orientation. According to such a configuration, a single supporting tool that has three types of fixation functions can be realized. In this case, the exterior of the supporting tool achieves two fixation functions, and the interior of the supporting tool achieves one fixation function. In this manner, with the use of both the outer form and the inner structure, multi-functionality is realized.

According to another aspect of the present invention, preferably, the X-ray measurement supporting tool is placed on an imaging stage during use, and is placed on a floor surface during non-use, to form a stepping base. With such a configuration, a supporting tool that further has a fourth function can be provided.

According to another aspect of the present invention, preferably, the first outer form has a first inclined surface and a second inclined surface arranged in a front-and-rear direction, the second outer form is formed on one of a right side end and a left side end of the X-ray measurement supporting tool, and the inner structure has an opening formed in the other one of the right side end and the left side end of the X-ray measurement supporting tool, and a measurement chamber in communication with the opening and provided between the first inclined surface and the second inclined surface. According to such a configuration, the entirety of the supporting tool can be skillfully used.

EMBODIMENT

A preferred embodiment of the present invention will now be described with reference to the drawings.

Figure 1:
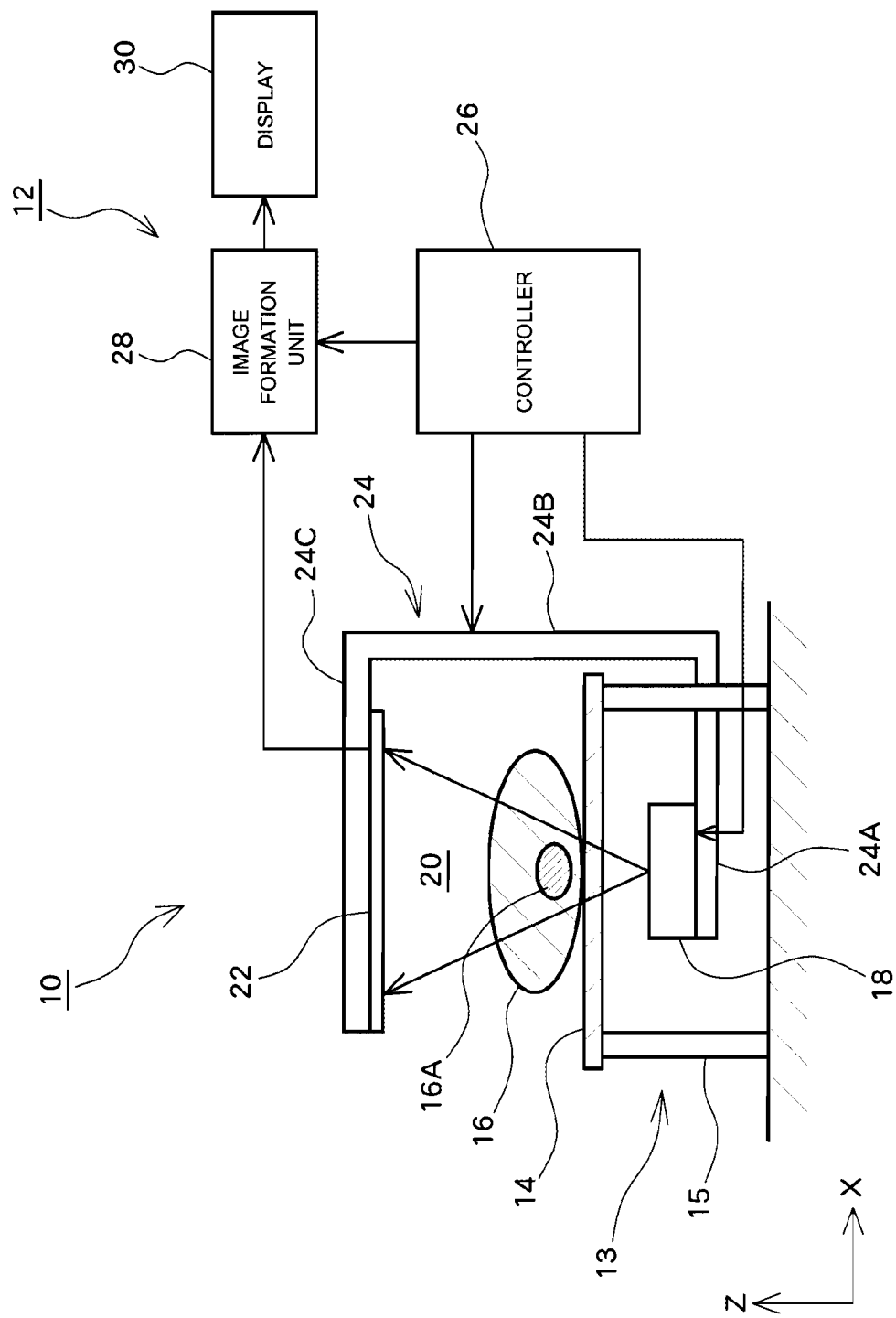
FIG. 1 is a block diagram showing a bone density measurement device to which an X-ray measurement supporting tool according to a preferred embodiment of the present invention is applied.

FIG. 1 is a block diagram of a bone evaluation device to which an X-ray measurement supporting tool (hereinafter simply referred to as a "supporting tool") according to a preferred embodiment of the present invention is applied. The bone density measurement device is a device which is placed in a medical institution, and which measures a bone density (bone mineral density) by radiating an X-ray on a lumbar spine, a femur, a radius, or the like of a human body as a subject. The supporting tool may be used in a general radiographic imaging, or in other measurements. As will be described below, the supporting tool according to the present embodiment is used to form a knee-bent orientation of both lower limbs, an inner side twisted orientation of the lower limbs, and a horizontal orientation of one arm. That is, the supporting tool has composite functions.

As seen in FIG. 1, the bone density measurement device comprises a measurement unit 10 and a control unit 12. The measurement unit 10 has a bed 13 placed on a floor surface, and the bed 13 has a mounting base (mounting plate) 14 and a leg unit 15 supporting the mounting base 14. On the mounting base 14 on the bed 13, a subject 16 is laid, for example, in a face-up orientation. Reference numeral 16A represents a measurement target bone, and is, for example, the lumbar spine. When the lumbar spine is to be measured, the legs are set in the knee-bent state such that the lumbar spine is in a naturally stretched-out state, and the supporting tool is inserted below the legs in order to form and maintain the knee-bent state. When the femur (s) of one or both legs is to be measured, the legs are set in a twisted state, and the supporting tool is used to maintain or fix the heels and toes of the legs for achieving the twisted state. When the forearm is to be measured, the forearm of the subject is placed on the mounting base 14 in a state where the subject is sitting on a chair. The supporting tool is used to position the arm and maintain the orientation of the arm. In the present embodiment, one supporting tool achieves functions to selectively form and maintain orientations of three sites.

An X-ray generator 18 is provided below the mounting base 14, and an X-ray detector 22 is provided above a subject storage space 20 on the mounting base 14. The X-ray generator 18 generates a fan-beam having a two-dimensional spreading shape as the X-ray beam in the example configuration shown in the figures. Alternatively, a cone-beam having a conical shape may be formed. The X-ray generator 18 alternately generates a high-energy X-ray and a low-energy X-ray. The X-ray detector 22 comprises a plurality of X-ray sensors placed one-dimensionally. Alternatively, a plurality of sensors arranged two-dimensionally may be used. Alternatively, a configuration may be employed in which the X-ray generator 18 is provided above the subject 16 and the X-ray detector 22 is provided below the subject 16. In the present embodiment, the X-ray generator 18 and the X-ray detector 22 are held by a slide mechanism 24. The slide mechanism 24 comprises an arm 24A extending in an X direction, a support column 24B extending in a Z direction, and an arm 24C extending in the X direction. The X-ray generator 18 is fixed on the arm 24A, and the X-ray detector 22 is fixed on the arm 24C. The slide mechanism 24 slides and moves in a Y direction which is a horizontal direction orthogonal to the X direction. Alternatively, a configuration may be employed in which the slide mechanism 24 can further slide and move in the X direction.

A controller 26 controls operations of the structures shown in FIG. 1. In particular, the controller 26 controls the operations of the X-ray generator 18 and the slide mechanism 24. An image formation unit 28 is a module that generates an image representing a two-dimensional distribution of a bone mineral density based on X-ray detection data. Such an image is displayed on a display 30. In addition, an average bone density or the like is also displayed on the display 30 as a numerical value.

Figure 2:
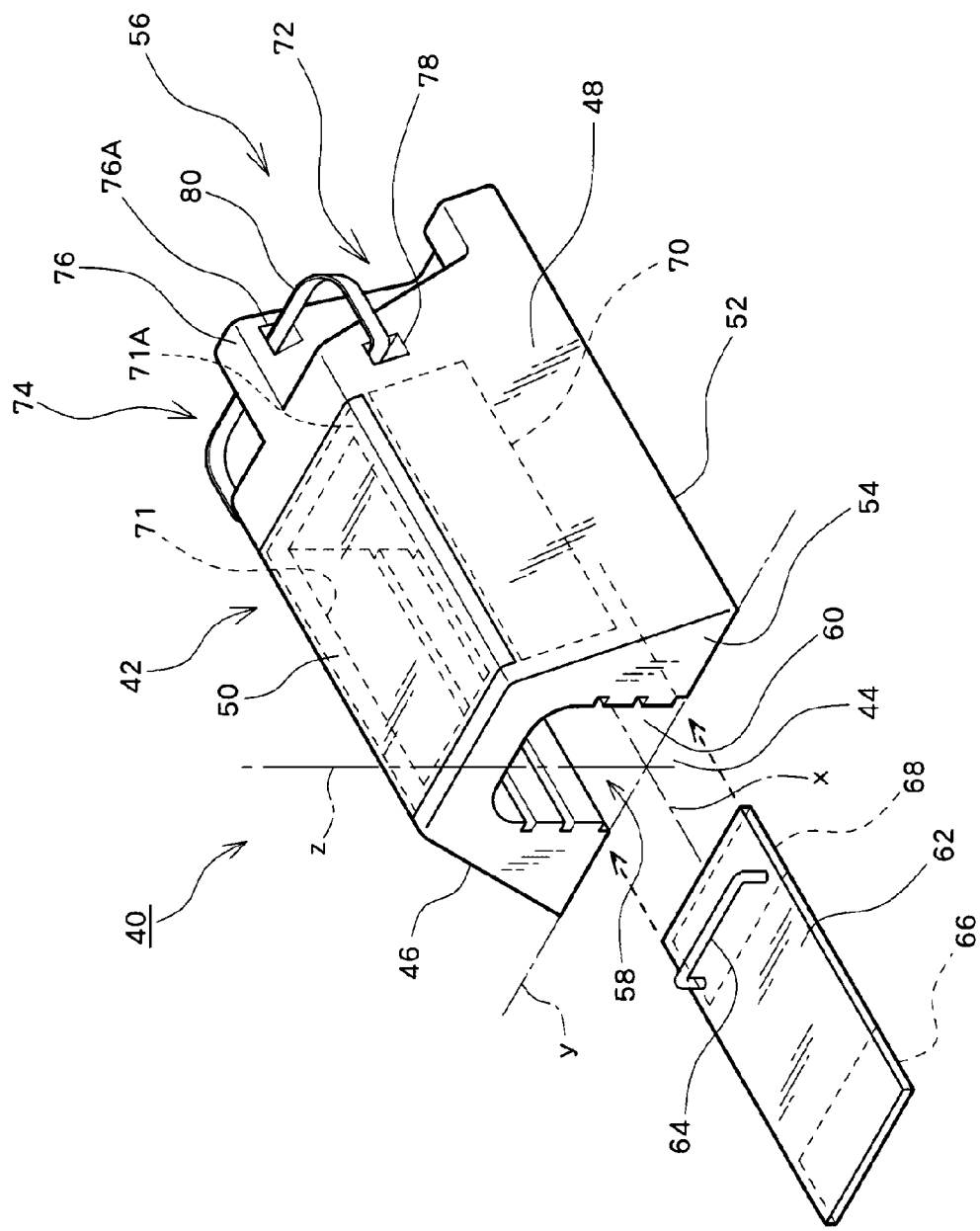
FIG. 2 is a perspective diagram showing a supporting tool according to a preferred embodiment of the present invention.

FIG. 2 is a perspective diagram of the supporting tool according to the present embodiment. The supporting tool 40 has a trapezoidal form in a yz plane, and an approximate rectangular form in an xz plane. The supporting tool 40 has an outer form 42 and an inner structure 44 for realizing a plurality of fixation functions. As will be described below in detail, the outer form 42 includes a first outer form for setting two legs in a knee-bent orientation, and a second outer form for setting the two legs in a twisted orientation.

The outer form 42 will now be described in detail. A body of the supporting tool 40 is made of an X-ray transmitting member such as a resin, and includes two inclined surfaces 46 and 48 arranged in a front-and-rear direction. The inclined surfaces 46 and 48 are used when the knee-bent orientation is formed. For example, back sides of thighs of two legs are caused to contact the inclined surface 46, and calves of two legs are caused to contact the inclined surface 48. Falling angles (inclination angles) of the inclined surfaces 46 and 48 are set, for example, in a range of 45 to 60 degrees. On an upper surface of the body of the supporting tool 40, a transparent top plate 50 is provided. The top plate 50 is also formed by an X-ray transmitting member, and is, for example, an acryl plate. The top plate 50 is a plate-shaped member extending in the xy plane direction. The body of the supporting tool 40 has a bottom surface 52. The bottom surface 52 is joined on the mounting base. A shielding plate that shields from a measurement X-ray is provided on the bottom surface 52. No such member is provided on a bottom surface of a measurement chamber 58 to be described later. The shielding plate is a radiation exposure reducing member that prevents transmission of the X-ray to sites other than the measurement site as much as possible.

An opening is formed on one end (end surface) 54 of the body of the supporting tool 40, and forms an entrance of the inner structure 44. The inner structure 44 has the measurement chamber 58 in communication with the opening. In other words, the measurement chamber 58 is a hollow space in the body of the supporting tool 40, and a bottom surface thereof is opened. A base plate 62 is set in the measurement chamber 58. More specifically, the measurement chamber 58 has a slit pair array 60 formed on front and rear inner wall surfaces, and the base plate is inserted to one of the slit pair. With such a configuration, the mounting height of the base plate 62 can be switched stepwise; that is, the magnification can be varied stepwise. The slit pair array 60 includes, for example, a lower slit pair, a middle slit pair, and an upper slit pair. Each individual slit pair includes two slits formed at the same height and opposing each other. The base plate 62 is formed by a member that weakens the measurement X-ray to a certain degree. With such a configuration, it is possible to prevent saturation at the X-ray detector during the forearm measurement. Two shielding plates 66 and 68 separated from each other in the x direction with an intermediate part therebetween are provided on the base plate 62. The shielding plates reduce radiation exposure of sites other than the sites to be measured. A handle (grip) 64 is provided on the base plate 62, and the handle 64 is gripped by the measurement target arm of the subject. In practice, the gripping is done in the measurement chamber 58. With the formation of such a gripping orientation, the measurement site can be positioned and fixed. When the handle 64 is gripped, the inside of the measurement chamber 58 can be observed through the top plate 50. Because the inside of the measurement chamber 58 can be observed, a feeling of safety can be given to the subject.

A shielding plate numeral is provided on an inner side of the inclined surface 46, and, similarly, a shielding plate 70 is provided on an inner side of the inclined surface 48. The shielding plates block a scattering X-ray generated in the measurement chamber 58 and leakage to the outside. When the measurement X-ray is radiated onto the bone, scattering X-rays are emitted from the bone in various directions. All or a part of the scattering X-ray is shielded by the plurality of shielding plates. Alternatively, the shielding plates may be provided on both end surfaces in the left-and-right direction of the measurement chamber. During the measurement of the forearm, if the scattering X-ray can be effectively shielded, radiation exposure of a body, a head, an arm on the other side, or the like of the subject can be reduced. Alternatively, the outer side of the body of the supporting tool 40 (for example, two inclined surfaces 46 and 48) maybe formed with a member having flexibility.

A side end structure 56 is provided on the other end of the body of the supporting tool 40, which is a structure that holds portions of two legs from the heel to the toe in a twisted orientation. Specifically, the side end structure 56 has a left leg holding unit 72 and a right leg holding unit 74. An intermediate wall 76 is provided between the holding units 72 and 74, a through path 78 extending in the y direction is formed on the other end of the supporting tool 40, a through path 76A is formed on the intermediate wall 76, and a belt 80 passing through the through paths is provided. The belt 80 is a member that maintains a state where two distant ends of two legs contact two inclined surfaces, as will be described later. A side from the heel toward the toe is fixed by the belt. Alternatively, a portion for holding the leg may be formed from an elastic material. Alternatively, the belt 80 maybe formed from an elastic material.

The top plate 50 is provided in a horizontal state to cover an opening 71 forming a ceiling surface of the measurement chamber 58. Specifically, the top plate 50 is placed on a base surface 71A formed around the opening 71.

Figure 3:
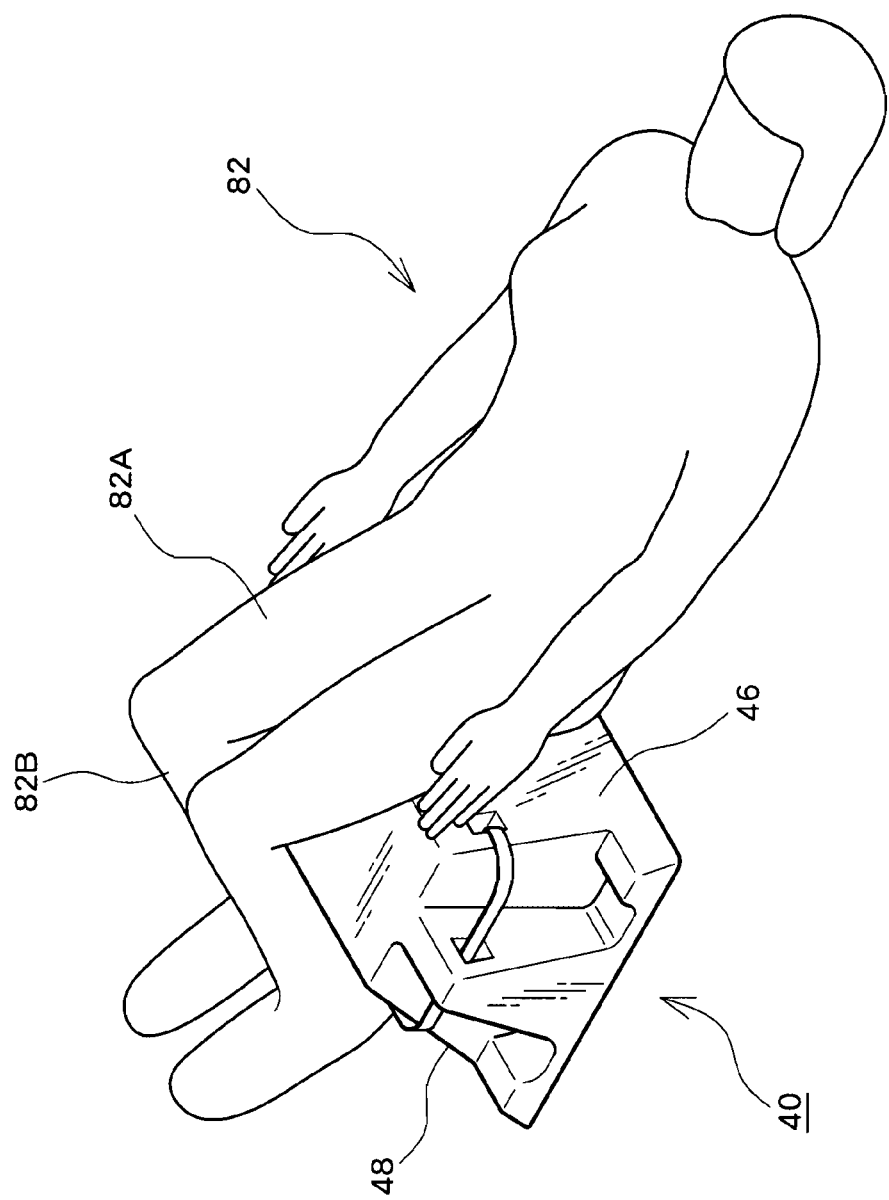
FIG. 3 is a diagram showing a first example use of the supporting tool shown in FIG. 2.

FIG. 3 shows a first example use of the supporting tool 40 shown in FIG. 2. When a lumbar spine of a subject 82 is to be measured, the supporting tool 40 is inserted below the two legs of the subject 82. Specifically, the supporting tool 40 is placed on the measurement base shown in FIG. 1. Back sides of thighs 82A of the legs are caused to contact the inclined surface 46, and back sides of below-knee sites 82B of the legs; that is, the calves, are caused to contact the inclined surface 48. The leg surfaces do not necessarily contact the two inclined surfaces 46 and 48, and the supporting tool 40 is used to form and maintain the knee-bent orientation. If such a knee-bent state is formed, the lumbar spine can be naturally stretched out, and a superior measurement condition with respect to the lumber can be formed. An alignment of the supporting tool 40 can be freely determined, and, in any case, the supporting tool 40 is placed such that the two inclined surfaces 46 and 48 are arranged along a body axial direction.

Alternatively, an elastic structure or the like may be provided between the below-knee part and the top plate as necessary. Alternatively, an orientation may be formed in which the below-knee part is raised further in an upper direction.

Figure 4:
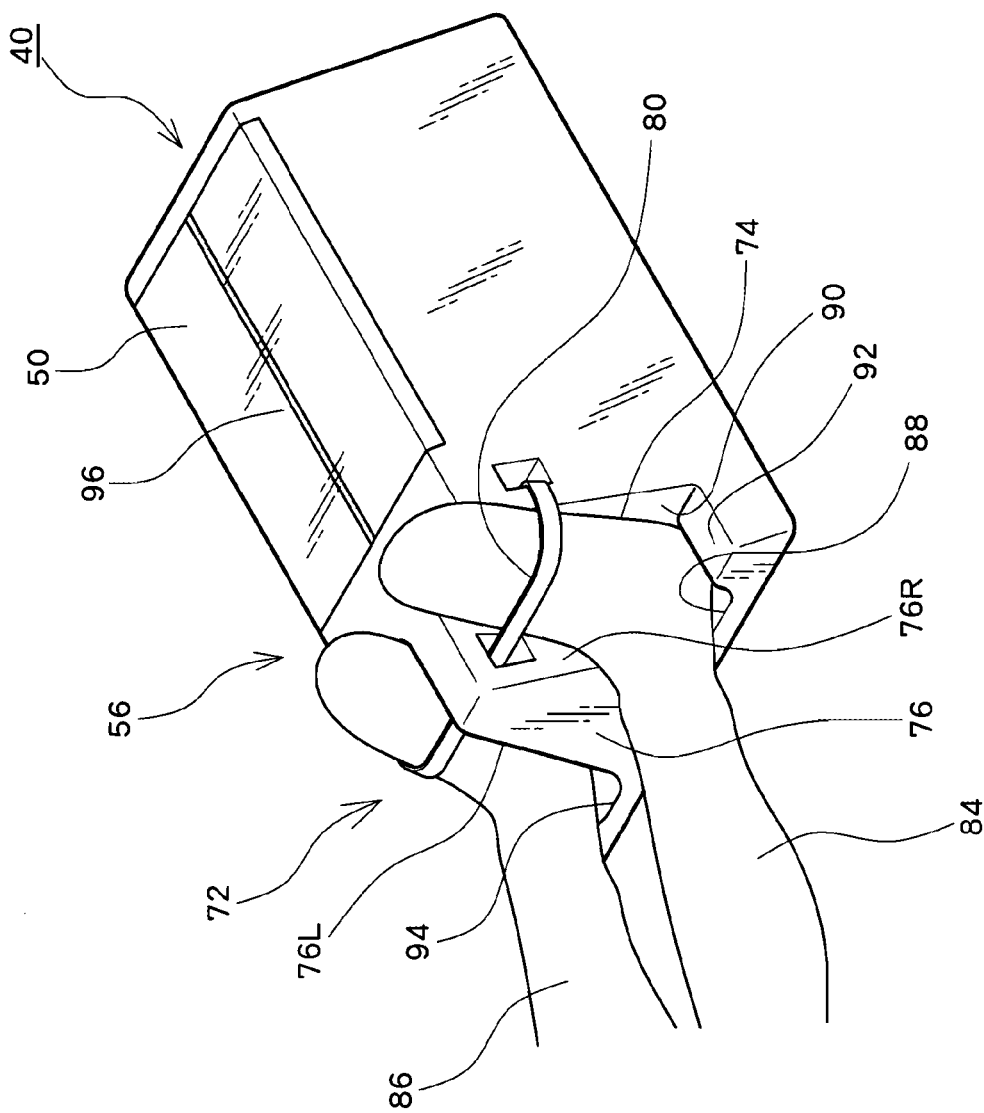
FIG. 4 is a diagram showing a second example use of the supporting tool shown in FIG. 2.

FIG. 4 shows a second example use of the supporting tool 40 shown in FIG. 2. When the femurs of two legs are to be measured, a twisted orientation of the two legs as shown in FIG. 4 is formed. More specifically, a distant end of a right leg 84 is housed in the right leg holding unit 74, and a distant end of a left leg 86 is housed in the left leg holding unit 72. In the right leg holding unit 74, a heel of the right leg 84 is placed within a recess 88, and the distant end is set in an orientation rotated toward the inner side such that an inner side surface from a region near the heel to the joint of the big toe is in close contact with an inclined surface 76R. In order to maintain such an orientation, a predetermined site from the heel toward the toe is tightened by the belt 80. A back side of the leg contacts a surface 90. Similarly, in the left leg holding unit 72 also, the heel is placed within a recess 94, and an inner side surface on the big toe side contacts an inclined surface 76L. This orientation is maintained by the belt 80. In this manner, because the leg holding structures are provided as the side end structure 56 in the supporting tool 40, the legs can be placed in proper orientations for the femur measurement.

Alternatively, a marker 96 serving as a center line may be provided on the top plate 50 having a transparent characteristic, as shown in FIG. 4. Such a marker 96 forms a reference line during measurement of the forearm. That is, by matching a center line of the forearm to the marker 96, the forearm can be positioned at a proper position. Alternatively, in the side end structure 56 of FIG. 4, a portion contacting the leg may be formed with a member having elasticity. Alternatively, the distant ends may be fixed not by the belt 80, but using other members.

Figure 5:
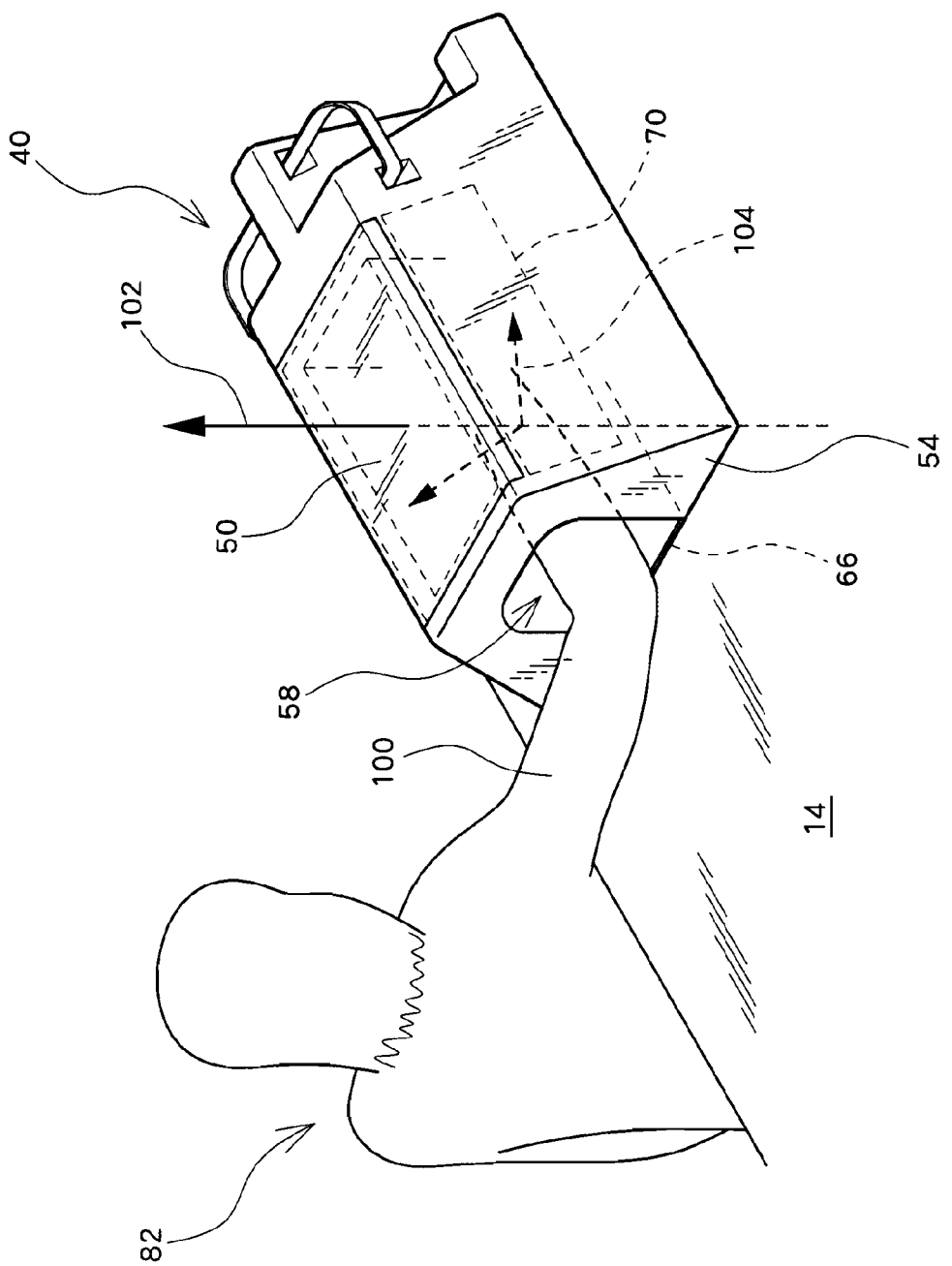
FIG. 5 is a diagram showing a third example use of the supporting tool shown in FIG. 2.

FIG. 5 shows a third example use of the supporting tool 40 shown in FIG. 2. In FIG. 5, the forearm is being measured; that is, the radius is being measured. The supporting tool 40 is placed on the mounting base 14, and a forearm portion of a right arm 100 of the subject 82 is inserted into the measurement chamber 58. More specifically, the handle is formed on the above-described base plate, and the forearm is positioned by the subject gripping and holding the handle. As shown in FIG. 5, when an X-ray 102 is radiated from below, a scattering X-ray 104 is caused at the bone part, but such a scattering X-ray 104 is shielded by the shielding plate 70. In other words, leakage of the scattering X-ray is prevented. This configuration achieves a radiation exposure reducing advantage of the subject 82. Because the base plate itself is formed from the X-ray weakening material, a certain weakening function is achieved with respect to the measurement X-ray 102, and, with such a configuration, saturation at the X-ray detector can be prevented in advance. Further, the shielding plate 66 is provided on both sides of the measurement site in the base plate, and radiation exposure with respect to sites in the forearm other than the measurement site is reduced. In such a measurement situation, because the top plate 50 is formed from a transparent member, the forearm can be accurately positioned, and, at the same time, a feeling of safety can be given to the subject 82 by observation of the measurement chamber 58.

Figure 6:
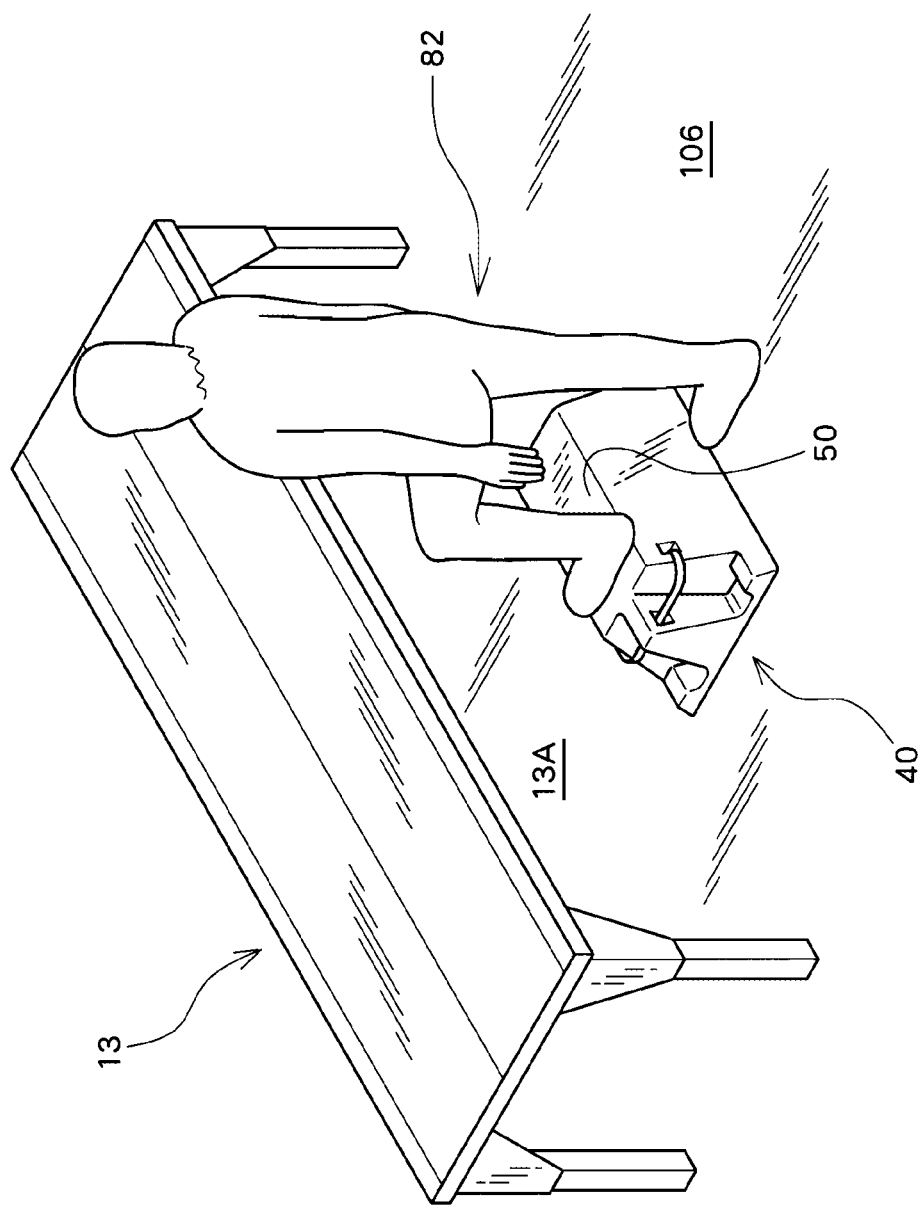
FIG. 6 is a diagram showing a fourth example use of the supporting tool shown in FIG. 2.

FIG. 6 shows a fourth example use of the supporting tool 40 shown in FIG. 2. In FIG. 6, the supporting tool 40 is placed near the bed 13; specifically, on a floor surface 106. By placing a leg on the top plate 50 of the supporting tool 40, it becomes easy for the subject 82 to move up onto the bed 13 using the supporting tool 40 as a stepping base. When the supporting tool 40 is not in use, the supporting tool 40 may be stored in a lower space 13A of the bed 13.

As described, according to the supporting tool of the present embodiment, with a single supporting tool, two lower limbs can be maintained in the knee-bent orientation, two lower limbs may be maintained in the twisted orientation, and the forearm can be positioned in the measurement of the forearm. In addition, the supporting tool may be used as a stepping base as necessary. Thus, multi-functionality can be achieved with a single supporting tool, and the usage value thereof can be significantly improved. In the related art, a plurality of types of supporting tools must be prepared corresponding to the measurement sites, but according to the present embodiment, basically, only a single supporting tool needs to be provided. Therefore, the space for storing the supporting tool can be reduced and the handling of the supporting tool can be greatly facilitated. Further, in the measurement of the forearm, unnecessary radiation exposure of the forearm can be prevented or reduced, and, at the same time, radiation exposure by the scattering X-ray can be prevented or reduced. The supporting tool of the present embodiment has a characteristic that the outer form and the inner structure are both used, and, in particular, a characteristic that two functions are achieved by the outer form. The supporting tool of the present embodiment can be modified in various ways.

The invention claimed is:

1. An X-ray measurement supporting tool, comprising:
   an outer form that maintains, when a first bone part of a subject is to be measured, a first limb of the subject in a first orientation; and
   an inner structure that maintains, when a second bone part of the subject is to be measured, a second limb of the subject in a second orientation.

2. The X-ray measurement supporting tool according to claim 1, wherein
   the first limb is a lower limb, and the second limb is an upper limb.

3. The X-ray measurement supporting tool according to claim 2, wherein
   the second bone part is a radius,
   the inner structure has a measurement chamber to which a forearm serving as the upper limb is inserted, and
   a scattering X-ray shielding member that blocks a scattering X-ray generated in the measurement chamber is provided on at least a part of a periphery of the measurement chamber.

4. The X-ray measurement supporting tool according to claim 2, wherein
   the inner structure has a base equipped with a grip gripped by the subject, and
   a measurement X-ray shielding member for preventing excessive radiation exposure is provided on an outside of a measurement region in the base.

5. The X-ray measurement supporting tool according to claim 4, wherein
   the inner structure has a height varying structure that allows a mounting height of the base to be varied.

6. The X-ray measurement supporting tool according to claim 3, wherein
   a transparent top plate is provided above the measurement chamber.

7. The X-ray measurement supporting tool according to claim 1, wherein
   the first bone part is a lumbar spine,
   the first orientation is a knee-bent orientation of a lower limb serving as the first limb, and
   the outer form has a form provided below the lower limb and supporting the knee-bent orientation of the lower limb.

8. The X-ray measurement supporting tool according to claim 7, further comprising:
   a first inclined surface that contacts a back side of a thigh of the subject in a state where the knee-bent orientation of the lower limb is supported; and
   a second inclined surface that contacts a calf of the subject in a state where the knee-bent orientation of the lower limb is supported.

9. The X-ray measurement supporting tool according to claim 8, wherein
   the X-ray measurement supporting tool has a vertical cross section of a trapezoid.

10. The X-ray measurement supporting tool according to claim 1, wherein
    the first bone part is a femur,
    the first limb is a lower limb, and
    the outer form comprises:
    a recess that houses a heel of the lower limb;
    an inclined surface to which an inner side surface of the lower limb from a region near an ankle to a joint of a big toe is caused to contact and that sets the lower limb in a twisted orientation; and
    a fixation member that fixes the lower limb in the twisted orientation from the heel toward a side of a toe.

11. The X-ray measurement supporting tool according to claim 1, wherein
    the first bone part is a left femur and a right femur,
    the first limb is a left lower limb and a right lower limb, and
    the outer form comprises:
    a first recess and a second recess that house a left heel and a right heel of the left lower limb and the right lower limb, respectively;
    a first inclined surface and a second inclined surface to which a left inner side surface and a right inner side surface of the left lower limb and the right lower limb from regions near a left ankle and a right ankle to joints of a left big toe and a right big toe are caused to contact, respectively, and that set the left lower limb and the right lower limb in a twisted orientation, respectively; and
    a first fixation member and a second fixation member that fix the left lower limb and the right lower limb in the twisted orientation from the left heel and the right heel toward a side of a left toe and a side of a right toe, respectively.

12. An X-ray measurement supporting tool, comprising:
a first outer form that maintains, when a lumbar spine of a subject is to be measured, a lower limb of the subject in a knee-bent orientation;
a second outer form that maintains, when a femur of the subject is to be measured, the lower limb of the subject in a twisted orientation; and
an inner structure that maintains, when an antebrachial bone of the subject is to be measured, a forearm of the subject in a horizontal orientation.

13. The X-ray measurement supporting tool according to claim 12, wherein
the X-ray measurement supporting tool is placed on an imaging stage during use, and is placed on a floor surface during non-use, to form a stepping base.

14. The X-ray measurement supporting tool according to claim 12, wherein
the first outer form has a first inclined surface and a second inclined surface arranged in a front-and-rear direction,
the second outer form is formed on one of a right side end and a left side end of the X-ray measurement supporting tool, and
the inner structure has an opening formed in the other one of the right side end and the left side end of the X-ray measurement supporting tool, and a measurement chamber in communication with the opening and provided between the first inclined surface and the second inclined surface.

* * * * *